(12) United States Patent
Werba et al.

(10) Patent No.: US 8,754,281 B2
(45) Date of Patent: *Jun. 17, 2014

(54) ENERGY CONSERVATION IN HEAVY-HYDROCARBON DISTILLATION

(75) Inventors: Gregory R. Werba, Arlington Heights, IL (US); Jason T. Corradi, Arlington Heights, IL (US); Zin X. Zhu, Long Grove, IL (US); David W. Ablin, Arlington Heights, IL (US); Saadet Ulas Acikgoz, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 241 days.

This patent is subject to a terminal disclaimer.

(21) Appl. No.: 12/868,309

(22) Filed: Aug. 25, 2010

(65) Prior Publication Data

US 2012/0048714 A1 Mar. 1, 2012

(51) Int. Cl.
C07C 7/04 (2006.01)
C07C 7/12 (2006.01)
C07C 15/08 (2006.01)
B01D 3/14 (2006.01)

(52) U.S. Cl.
USPC .......... 585/805; 203/25; 203/27; 203/74; 203/DIG. 8; 208/310 R; 208/353; 585/825; 585/826; 585/828

(58) Field of Classification Search
USPC ............ 203/25, 27, 41, 74, DIG. 8; 585/805, 585/820, 825, 826, 828, 910; 208/310 R, 208/353
See application file for complete search history.

(56) References Cited

U.S. PATENT DOCUMENTS

| | | | | |
|---|---|---|---|---|
| 2,528,892 A * | 11/1950 | Lien et al. | ...................... | 585/800 |
| 3,254,024 A * | 5/1966 | Huckins, Jr. et al. | ........... | 203/25 |
| 3,639,497 A * | 2/1972 | Martel et al. | ................... | 585/804 |
| 3,813,452 A * | 5/1974 | Bieser | ........................... | 585/479 |
| 3,844,902 A * | 10/1974 | Vickers et al. | .................. | 203/46 |
| 4,555,311 A * | 11/1985 | Ward | .............................. | 203/21 |
| 4,621,681 A * | 11/1986 | Grover | ........................... | 165/47 |
| 4,715,433 A * | 12/1987 | Schwarz et al. | .............. | 165/110 |
| 4,824,527 A | 4/1989 | Erickson | | |
| 5,401,476 A * | 3/1995 | Hotier et al. | .................. | 422/222 |
| 6,171,449 B1 * | 1/2001 | Welch | .......................... | 202/154 |
| 6,263,700 B1 * | 7/2001 | Agrawal et al. | ................. | 62/646 |
| 6,479,720 B1 * | 11/2002 | O'Brien et al. | ............... | 585/448 |
| 7,249,469 B2 | 7/2007 | Porter | | |
| 7,371,912 B2 * | 5/2008 | Schultz et al. | ................. | 585/478 |
| 7,687,674 B2 * | 3/2010 | Wegerer | ........................ | 585/477 |
| 8,030,533 B2 * | 10/2011 | Hotier et al. | ................... | 585/470 |
| 8,128,787 B2 * | 3/2012 | Wynn et al. | ..................... | 203/12 |
| 8,198,502 B2 * | 6/2012 | Bresler et al. | .................. | 585/805 |
| 2006/0162912 A1 * | 7/2006 | Prasad Nigam | .............. | 165/159 |
| 2010/0305380 A1 * | 12/2010 | Frey et al. | ..................... | 585/478 |

OTHER PUBLICATIONS

Cheng et al., Heat-Integrated Distillation Columns for Ternary Separations, Ind. Eng. Chem. Process Des. Dev. 1985, 24, pp. 707-713.

* cited by examiner

*Primary Examiner* — Virginia Manoharan
(74) *Attorney, Agent, or Firm* — Mark R Willis

(57) ABSTRACT

An aromatics complex producing one or more xylene isomers offers a large number of opportunities to conserve energy by heat exchange within the complex. One previously unrecognized opportunity is through providing two parallel distillation columns operating at different pressures to separate $C_8$ aromatics from $C_9$+ aromatics. The parallel columns offer additional opportunities to conserve energy within the complex through heat exchange in associated xylene recovery facilities.

10 Claims, 6 Drawing Sheets

US 8,754,281 B2

ENERGY CONSERVATION IN HEAVY-HYDROCARBON DISTILLATION

FIELD OF THE INVENTION

This invention relates to an improved process for energy savings in the distillation of hydrocarbons. More specifically, the present invention concerns energy conservation within an aromatics-processing complex producing xylene isomers.

BACKGROUND OF THE INVENTION

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

An aromatics complex flow scheme has been disclosed by Meyers in the Handbook of Petroleum Refining Processes, 2d. Edition in 1997 by McGraw-Hill, and is incorporated herein by reference.

Aromatics complexes producing xylenes are substantial consumers of energy, notably in distillation operations to prepare feedstocks and separate products from conversion processes. The separation of xylenes from heavy aromatics in particular offers substantial potential for energy savings. Energy conservation in such processes would not only reduce processing costs but also would address current concerns about carbon emissions.

SUMMARY OF THE INVENTION

A broad embodiment of the present invention comprises a distillation process comprising two or more xylene columns separating $C_8$-aromatics streams from a $C_9$-and-heavier aromatics streams contained in at least one lower-boiling and at least one higher-boiling feed stream, wherein the at least one higher-boiling feed stream has a higher content of $C_9$-and-heavier aromatics than the at least one lower-boiling feed stream, comprising distilling the at least one lower-boiling feed stream in at least one first xylene column at an elevated pressure to separate a first $C_8$-aromatics streams from a first $C_9$-and-heavier aromatics stream, distilling the at least one higher-boiling feed stream in at least one second xylene column at a low pressure column to separate a second $C_8$-aromatics stream from a second $C_9$-and-heavier aromatics stream, and condensing an overhead stream from the at least one first column by exchanging heat with one or both of a reboiler of the second column and a steam generator.

A more specific embodiment comprises a distillation process comprising two xylene columns separating $C_8$-aromatics streams from $C_9$-and-heavier aromatics streams contained in at least one lower-boiling and at least one higher-boiling feed stream, wherein the at least one higher-boiling feed stream has a higher content of $C_9$-and-heavier aromatics than the at least one lower-boiling feed stream, comprising distilling the at least one lower-boiling feed stream in at least one first xylene column at an elevated pressure to separate a first $C_8$-aromatics streams from a first $C_9$-and-heavier aromatics stream, distilling the at least one higher-boiling feed stream in at least one second xylene column at a low pressure column to separate a second $C_8$-aromatics stream from a second $C_9$-and-heavier aromatics stream, and condensing an overhead stream from the at least one first column by exchanging heat with a reboiler of the second column.

An alternative embodiment comprises a distillation process comprising two xylene columns separating $C_8$-aromatics streams from $C_9$-and-heavier aromatics streams contained in at least one lower-boiling and at least one higher-boiling feed stream, wherein the at least one higher-boiling feed stream has a higher content of $C_9$-and-heavier aromatics than the at least one lower-boiling feed stream, comprising distilling the at least one lower-boiling feed stream in at least one first xylene column at an elevated pressure to separate a first $C_8$-aromatics streams from a first $C_9$-and-heavier aromatics stream, distilling the at least one higher-boiling feed stream in at least one second xylene column at a low pressure column to separate a second $C_8$-aromatics stream from a second $C_9$-and-heavier aromatics stream, and condensing an overhead stream from the at least one first column Additional objects, embodiments and details of this invention can be obtained and inferred from the following detailed description of the invention.

DETAILED DESCRIPTION OF THE INVENTION

The feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feed stream to the process of the invention may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feed stream is catalytic reformate, the reformer preferably is operated at high severity to achieve high aromatics yield with a low concentration of nonaromatics in the product.

Figure 1:
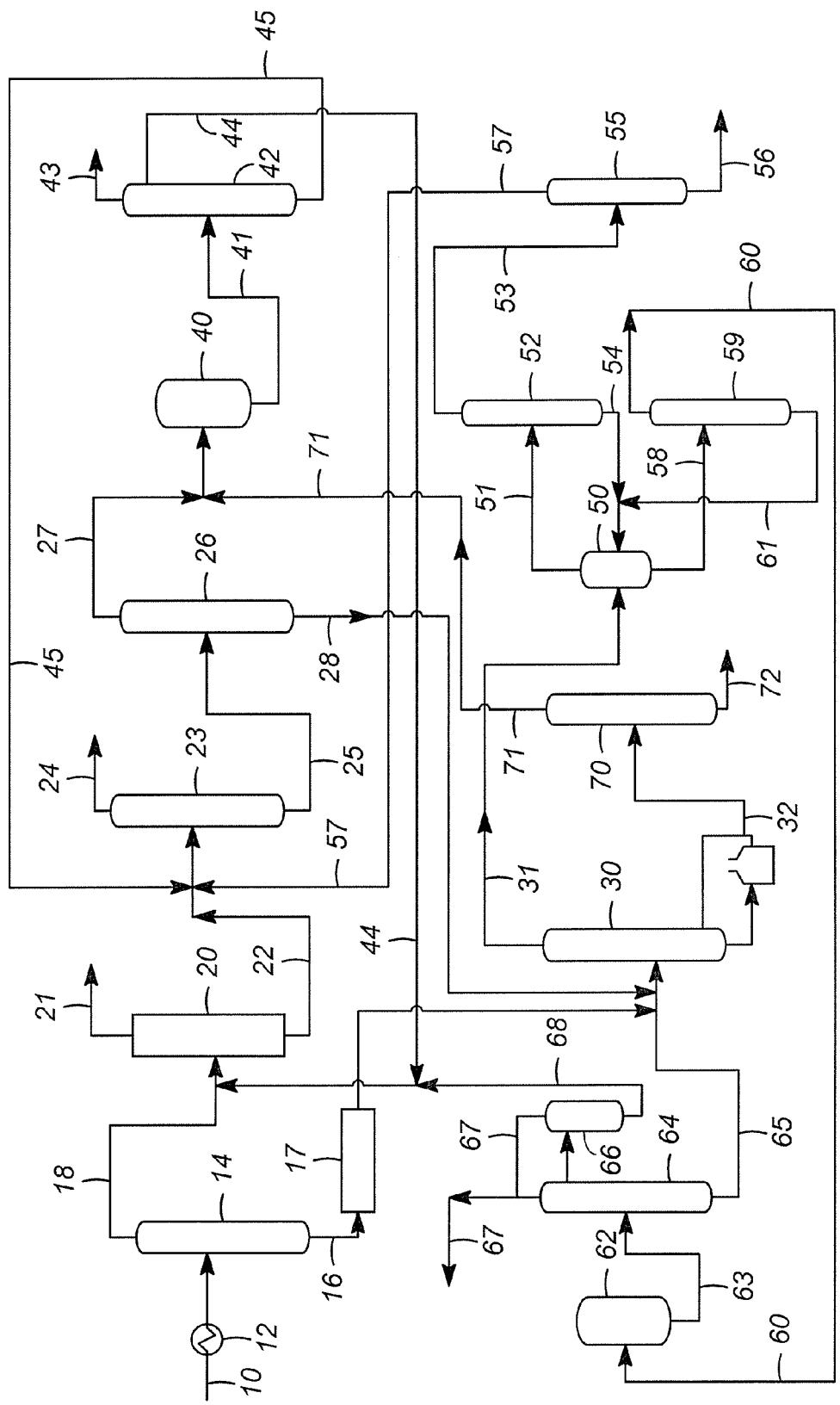
FIG. 1 schematically illustrates an aromatics complex in which energy-savings concepts could be applied.

FIG. 1 is a simplified flow diagram of a typical aromatics-processing complex of the known art directed to the production of at least one xylene isomer. The complex may process an aromatics-rich feed which has been derived, for example, from catalytic reforming. Usually such a stream will have been treated to remove olefinic compounds and light ends, e.g., butanes and lighter hydrocarbons and preferably pentanes; such removal, however, is not essential to the practice of the broad aspects of this invention. The aromatics-containing feed stream contains benzene, toluene and $C_8$ aromatics and typically contains higher aromatics and aliphatic hydrocarbons including naphthenes.

The feed stream is passed via conduit 10 via a heat exchanger 12 to reformate splitter 14 and distilled to separate a stream comprising $C_8$ and heavier aromatics, withdrawn as a bottoms stream in conduit 16, from toluene and lighter hydrocarbons recovered overhead via conduit 18. The toluene and lighter hydrocarbons are sent to extractive distillation process unit 20 which separates a largely aliphatic raffinate in conduit 21 from a benzene-toluene aromatics stream in conduit 22. The aromatics stream in conduit 22 is separated, along with stripped transalkylation product in conduit 45 and overhead from para-xylene finishing column in conduit 57, in benzene column 23 into a benzene stream in conduit 24 and a toluene-and-heavier aromatics stream in conduit 25 which is sent to a toluene column 26. Toluene is recovered overhead from this column in conduit 27 and may be sent partially or totally to a transalkylation unit 40 as shown and discussed hereinafter.

A bottoms stream from the toluene column 26 is passed via conduit 28, along with bottoms from the reformate splitter in conduit 16, after treating via clay treater 17, and recycle $C_8$ aromatics in conduit 65, to xylene column 30. The fractionator 30 separates concentrated $C_8$ aromatics as overhead in conduit 31 from a high-boiling stream comprising $C_9$, $C_{10}$ and heavier aromatics as a bottoms stream in conduit 32. This bottoms stream is passed in conduit 32 to heavy-aromatics column 70. The heavies column provides an overhead stream in conduit 71 containing $C_9$ and at least some of the $C_{10}$ aromatics, with higher boiling compounds, primarily $C_{11}$ and higher alkylaromatics, being withdrawn as a bottoms stream via conduit 72.

The $C_9+$ aromatics from heavies column in conduit 71 is combined with the toluene-containing overhead contained in conduit 27 as feed to transalkylation reactor 40, which contains a transalkylation catalyst as known in the art to produce a transalkylation product comprising benzene through $C_{11}+$ aromatics with xylenes as the focus. The transalkylation product in conduit 41 is stripped in stripper 42 to remove gases in conduit 43 and $C_6$ and lighter hydrocarbons which are returned via conduit 44 to extractive distillation 20 for recovery of light aromatics and purification of benzene. Bottoms from the stripper are sent in conduit 45 to benzene column 23 to recover benzene product and unconverted toluene.

The $C_8$-aromatics overhead provided by fractionator 30 contains para-xylene, meta-xylene, ortho-xylene and ethylbenzene and passes via conduit 31 to para-xylene separation process 50. The separation process operates, preferably via moving-bed adsorption using a desorbent, to provide a mixture of para-xylene and desorbent via conduit 51 to extract column 52, which separates para-xylene via conduit 53 from returned desorbent in conduit 54; the para-xylene is purified in finishing column 55, yielding a para-xylene product via conduit 56 and light material which is returned to benzene column 23 via conduit 57. A non-equilibrium mixture of $C_8$-aromatics raffinate and desorbent from the separation process 50 is sent via conduit 58 to raffinate column 59, which separates a raffinate for isomerization in conduit 60 from returned desorbent in conduit 61.

The raffinate, comprising a non-equilibrium mixture of xylene isomers and ethylbenzene, is sent via conduit 60 to isomerization reactor 62. The raffinate is isomerized in reactor 62, which contains an isomerization catalyst to provide a product approaching equilibrium concentrations of $C_8$-aromatic isomers. The product is passed via conduit 63 to deheptanizer 64, which removes $C_7$ and lighter hydrocarbons with bottoms passing via conduit 65 to xylene column 30 to separate $C_9$ and heavier materials from the isomerized $C_8$-aromatics. Overhead liquid from deheptanizer 64 is sent to stripper 66, which removes light materials overhead in conduit 67 from $C_6$ and $C_7$ materials which are sent via conduit 68 to the extractive distillation unit 20 for recovery of benzene and toluene values.

There are many possible variations of this scheme within the known art, as the skilled routineer will recognize. For example, the entire $C_6$-$C_8$ reformate or only the benzene-containing portion may be subjected to extraction. Para-xylene may be recovered from a $C_8$-aromatic mixture by crystallization rather than adsorption. Meta-xylene as well as para-xylene may be recovered from a $C_8$-aromatic mixture by adsorption, and ortho-xylene may be recovered by fractionation. Alternatively, the $C_9$-and heavier stream or the heavy-aromatics stream is processed using solvent extraction or solvent distillation with a polar solvent or stripping with steam or other media to separate highly condensed aromatics as a residual stream from $C_9+$ recycle to transalkylation. In some cases, the entire heavy-aromatic stream may be processed directly in the transalkylation unit. The present invention is useful in these and other variants of an aromatics-processing scheme, aspects of which are described in U.S. Pat. No. 6,740,788 which is incorporated herein by reference.

The separation of $C_8$ aromatics from heavy aromatics in fractionator 30 is a situation in which the distillation process of the invention generally is effective. A distillation process of the present invention is represented by two or more xylene columns each effecting substantially the same separation between $C_8$ and $C_9+$ aromatics contained in two or more internal or external-feed streams of the aromatics complex designated respectively as a first and a second feed streams. Preferably the two streams comprise a first feed stream which is higher-boiling and a second feed stream which is lower-boiling, wherein the higher-boiling first feed stream has a higher content of $C_9+$ hydrocarbons than the second feed stream. The invention comprises distilling the first feed stream in at least one first fractionation column at a low pressure to separate a first $C_8$-aromatics stream from a first $C_9$-and-heavier aromatics stream, distilling the second feed stream in a second fractionation column at an elevated pressure to separate a second $C_8$-aromatics stream from a second $C_9$-and-heavier aromatics stream, and circulating an overhead stream from the second column to provide heat to a reboiler of the first column. The low pressure typically is between 100 and 800 kPa and the elevated pressure is chosen to enable heat transfer from the first column to the second and typically is at least about 400 kPa above the low pressure. This concept of different pressures in parallel columns is particularly valuable when the heavy components present in the higher-boiling feed stream are subject to degradation at reboiler temperatures needed to separate the light and heavy components.

The second fractionation column processes a second feed stream with a lower concentration of heavy materials subject to decomposition than the feed to the first column, and the pressure thus may be raised higher in order to effect energy savings through heat exchange between the first and second columns without loss of product yield or risk of equipment fouling. This feed preferably comprises most or all of the isomerized $C_8$ aromatics from the isomerization reactor following deheptanization, but may also comprise other $C_8$-aromatic streams with low concentrations of heavy aromatics. This stream to the second column typically contains less than about 10 weight-% $C_9$+ aromatics, more often less than about 5 weight-% $C_9$+ aromatics, and frequently less than about 2 weight-% $C_9$+ aromatics. Effectively, the process comprises operating the second column at a pressure that would enable the overhead to provide heat to a reboiler of the first column and, preferably, a reboiler of at least one other column and/or steam generator in an associated processing complex.

In another embodiment, the process comprises operating the second fractionation column at a pressure that would enable the overhead to provide heat to generate steam useful in an associated processing complex. Further, the $C_8$-aromatics fractionator may comprise three or more columns comprising additional heat exchange between overheads and reboilers in an analogous manner to the above description.

Figure 2:
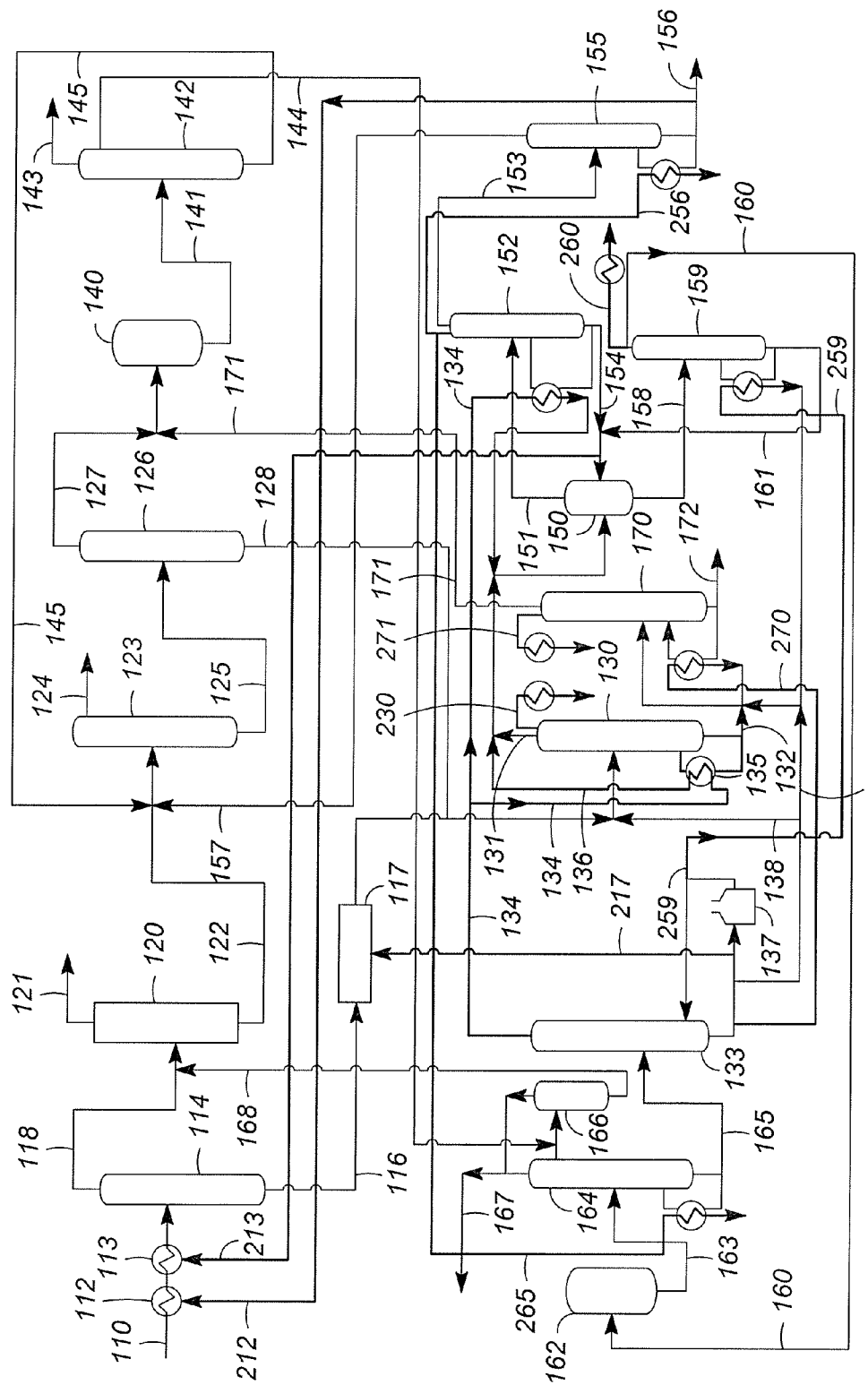
FIG. 2 illustrates an aromatics complex in which energy conservation is applied.

FIG. 2 is an energy-efficient aromatics complex employing a number of concepts of the invention. For ease of reference, a parallel numbering system is employed to those of FIGS. 1 and 2. The feed stream is passed via conduit 110 via heat exchangers 112 and 113, which raise the temperature of the feed stream, to reformate splitter 114. The heat exchange is supplied via conduits 212 and 213 respectively from the net para-xylene product and the recovered desorbent from the para-xylene separation process as discussed later in this section.

As in FIG. 1, $C_8$ and heavier aromatics are withdrawn as a bottoms stream in conduit 116 while toluene and lighter hydrocarbons recovered overhead via conduit 118 are sent to extractive distillation process unit 120 which separates a largely aliphatic raffinate in conduit 121 from a benzene-toluene aromatics stream in conduit 122. The aromatics stream in conduit 122 is separated, along with stripped transalkylation product in conduit 145 and overhead from para-xylene finishing column in conduit 157, in fractionator 123 into a benzene stream in conduit 124 and a toluene-and-heavier aromatics stream in conduit 125 which is sent to a toluene column 126. Toluene is recovered overhead from this column in conduit 127 and may be sent partially or totally to a transalkylation unit 140 as shown and discussed hereinafter.

A bottoms stream from the toluene column 126 is passed via conduit 128, along with bottoms from the reformate splitter in conduit 116, after treating via clay treater 117, and a purge stream of heavy aromatics in conduit 138, to low-pressure first xylene column 130. The feed stream to this column is characterized as a higher-boiling feed stream, as it generally contains more than about 5 weight-% $C_9$+ aromatics and often more than about 10 weight-% $C_9$+ aromatics. Other C8-aromatics streams having significant contents of $C_9$ and heavier aromatics, including streams obtained from sources outside the complex, also may be added to this higher-boiling feed stream; a portion of deheptanizer bottoms in stream 165 also may be included depending on overall energy balances. The low-pressure xylene column separates concentrated first $C_8$-aromatics stream as overhead in conduit 131 from a high-boiling first $C_9$-and-heavier stream comprising $C_9$, $C_{10}$ and heavier aromatics as a bottoms stream in conduit 132.

Simultaneously, an isomerized $C_8$-aromatics stream is passed via conduit 165 to a high-pressure second xylene column 133. This is characterized as a lower-boiling feed stream which contains a lower concentration of heavy materials subject to decomposition than the feed to column 130, and the column pressure thus can be increased in order to effect energy savings. Other $C_8$-aromatics-containing streams having similarly low contents of $C_9$-and-heavier aromatics, including streams obtained from sources outside the complex, also may be contained in the feed stream to this column. The second xylene column separates a second $C_8$-aromatics stream as overhead in conduit 134 from a second $C_9$-and-heavier stream in conduit 132. At least a portion of overhead vapor from the high-pressure xylene column in conduit 134 preferably is employed to reboil low-pressure xylene column 130 in reboiler 135, leaving as a condensed liquid to the xylene-separation process 150 in conduit 136 as well as reflux (not shown) to column 133. In addition, the overhead in conduit 134 may be used to provide energy to the reboiler of extract column 152 or other such services which are described later or will be apparent to the skilled routineer.

The $C_9$+ bottoms stream passing to reboiler 137 may provide energy via one or both of the stream before the reboiler in conduit 270 and the heated stream from the reboiler in conduit 259 for reboiling respectively one or both of heavy-aromatics column 170 and raffinate column 159; the bottoms stream after heat exchange would be sent to the heavy-aromatics column 170. Other similar heat-exchange services will be apparent to the skilled routineer. The net bottoms stream in conduit 138 usually is passed through column 130 or may be in conduit 139 combined directly with the stream in conduit 132 to heavies column 170. The heavies column provides an overhead a stream in conduit 171 containing $C_9$ and at least some of the $C_{10}$ aromatics, with higher boiling compounds, primarily $C_{11}$ and higher alkylaromatics, being withdrawn as a bottoms stream via conduit 172. This column may be reboiled by xylene column bottoms in conduit 270, as discussed above. Overhead vapor from columns 130 and 170 also may generate steam respectively via conduits 230 and 271 as indicated, with condensed liquids either serving as reflux to each column or as net overhead respectively in streams 131 or 171.

The $C_9$+ aromatics from heavies column in conduit 171 is combined with the toluene-containing overhead contained in conduit 127 as feed to transalkylation reactor 140 to produce a transalkylation product containing xylenes. The transalkylation product in conduit 141 is stripped in stripper 142 to remove gases in conduit 143 and $C_7$ and lighter liquids which are returned via conduit 144 to extractive distillation 120 for recovery of light aromatics following stabilization in isomerate stripper 166. Bottoms from the stripper are sent in conduit 145 to benzene column 123 to recover benzene product and unconverted toluene.

The first and second $C_8$-aromatics streams provided by xylene columns 130 and 133, containing para-xylene, meta-xylene, ortho-xylene and ethylbenzene, pass via conduit 131 and 136 to xylene-isomer separation process 150. The description herein may be applicable to the recovery of one or more xylene isomers other than para-xylene; however, the description is presented for para-xylene for ease of understanding. The separation process operates via a moving-bed adsorption process to provide a first mixture of para-xylene and desorbent via conduit 151 to extract column 152, which separates para-xylene via conduit 153 from returned desorbent in conduit 154. Extract column 152 preferably is operated at an elevated pressure, at least about 300 kPa and more preferably about 500 kPa or higher, such that the overhead from the column is at sufficient temperature to reboil finishing column 155 via conduit 256 or deheptanizer 164 via conduit 265. Heat supplied for reboiling duty via conduits 256 and 265 results in the condensation of the extract in these streams which is either or both refluxed to column 152 (not shown) or sent as a net stream in conduit 153 to finishing column 155. The para-xylene is purified in finishing column 155, yielding a para-xylene product via conduit 156 and light material which is returned to benzene column 123 via conduit 157.

A second mixture of raffinate, as a non-equilibrium blend of $C_8$ aromatics, and desorbent from separation process 150 is sent via conduit 158 to raffinate column 159, which separates a raffinate to isomerization in conduit 160 from returned desorbent in conduit 161. The raffinate column may be operated at higher pressure to generate steam via conduit 260 or to exchange heat in other areas of the complex; condensed liquids from such heat exchange either serve as reflux to the raffinate column or as net overhead in conduit 160. Recovered desorbent in conduits 154 and 161 and net finishing column bottoms may heat the incoming feed stream in conduit 110 via conduits 213 and 212, respectively.

The raffinate, comprising a non-equilibrium blend of xylene isomers and ethylbenzene, is sent via conduit 160 to isomerization reactor 162. In the isomerization reactor 162, raffinate is isomerized to provide a product approaching equilibrium concentrations of $C_8$-aromatic isomers. The product is passed via conduit 163 to deheptanizer 164, which removes $C_7$ and lighter hydrocarbons and preferably is reboiled using overhead in conduit 265 from extract column 152. Bottoms from the deheptanizer passes via conduit 165 to xylene column 133 to separate $C_9$ and heavier materials from the isomerized $C_8$-aromatics. Overhead liquid from deheptanizer 164 is sent to stripper 166, which separates light materials overhead in conduit 167 from $C_6$ and $C_7$ materials which are sent via conduit 168 to the extractive distillation unit 120 for recovery and purification of benzene and toluene values. Pressures of deheptanizer 164 and stripper 166 are selected to exchange heat or generate steam in a manner analogous to the xylene columns discussed elsewhere in this specification.

Figure 3:
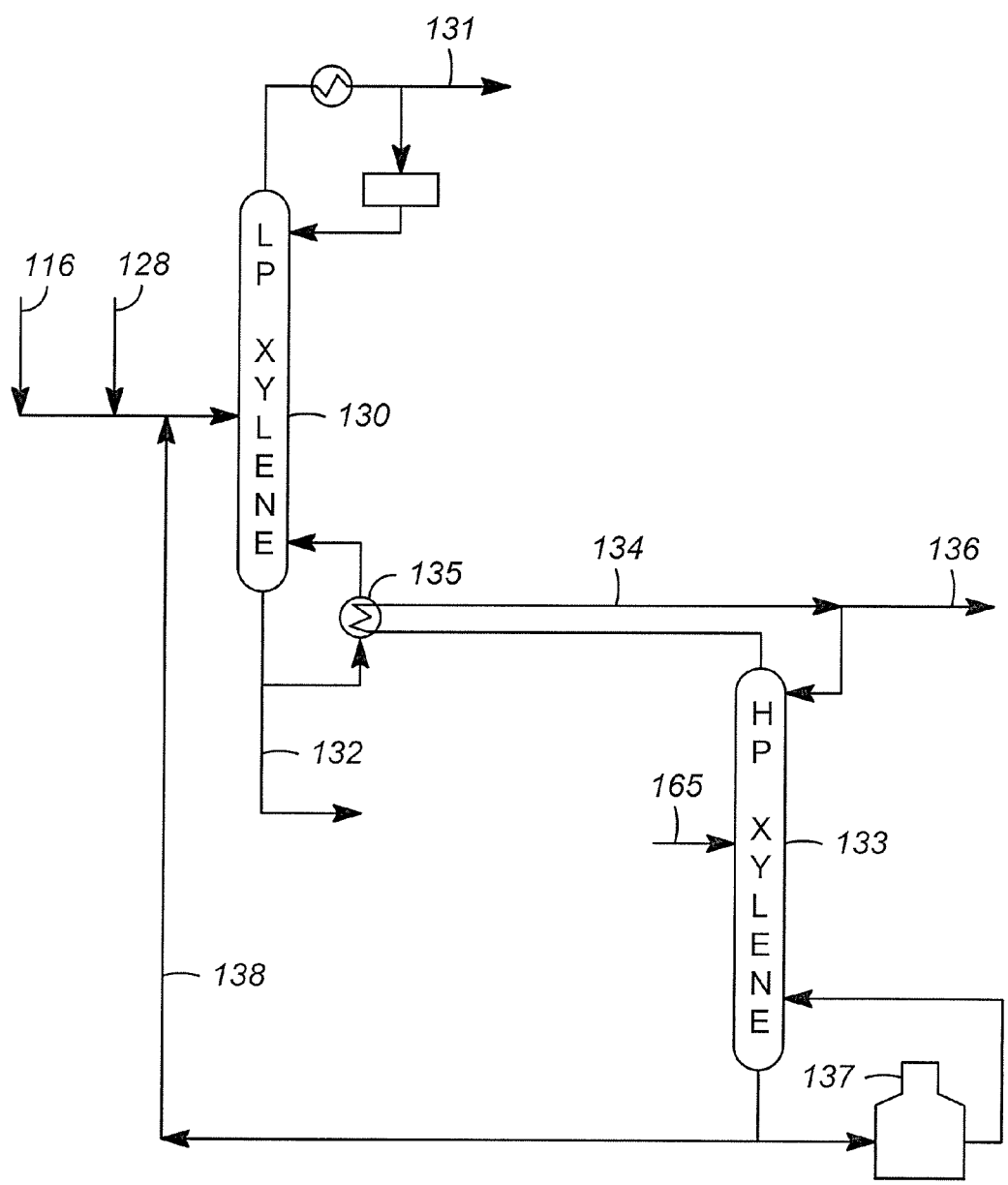
FIG. 3 shows the application of energy conservation in the distillation of $C_8$ aromatics from heavy aromatics.

FIG. 3 shows in more detail the heat exchange of the invention between parallel xylene distillation columns 130 and 133. Feed to the low-pressure xylene column 130 comprises bottoms from the toluene column via conduit 128, clay-treated bottoms from the reformate splitter in conduit 116, and purge $C_8$ aromatics in conduit 138 and may comprise other $C_8$-aromatics-containing streams not suitable for processing in the high-pressure xylene column as well as a portion of the deheptanized stream 165 if appropriate for energy balances. The combined feeds of heavy reformate and toluene-column bottoms may contain heavy aromatics which are susceptible to degradation at high temperatures, and operating at a pressure lower than 800 kPa permits temperatures to be maintained in the bottom of the column and reboiler which avoid such decomposition. The low-pressure xylene column separates concentrated $C_8$ aromatics as overhead in conduit 131 from a high-boiling stream comprising $C_9$, $C_{10}$ and heavier aromatics as a bottoms stream in conduit 132. The overhead stream from column 130 may be used at least partially via conduit 230 of FIG. 2 to generate steam or reboil other columns as discussed previously and thus be condensed to provide reflux to the column as well as the net overhead to xylene separation in conduit 131.

Simultaneously, an isomerized $C_8$-aromatics stream is passed via conduit 165 to high-pressure xylene column 133; this stream contains a lower concentration of heavy materials subject to decomposition than the feed to column 130; the column pressure is elevated with respect to that of the low-pressure xylene column according to the invention, as discussed previously, in order to effect energy savings through concomitantly higher temperatures which may be employed to exchange heat at useful levels. The temperature of the overhead vapor from the high-pressure xylene column 133 therefore is sufficient to provide useful energy to other services in an aromatics complex. As shown, the temperature of the overhead vapor is sufficient to reboil the low-pressure xylene column 130 in reboiler 135 as well as the reboiler of extract column 152, a condensed stream returning as reflux to column 133 (not shown) and a net stream in conduit 136 to xylenes separation. A small net bottoms stream in conduit 138 preferably is sent to low-pressure column 130 for recovery of remaining $C_8$ aromatics.

Alternatively or in addition, the temperature of overhead vapor from high-pressure xylene column 133 is sufficient to generate steam useful for heating services or to reboil columns in other processing units. Such steam is generated usually at a pressure of in excess of about 300 kPa, preferably at least about 500 kPa, and most preferably about 1000 kPa or higher. The overhead stream may be indirectly heat exchanged with a water circuit which feeds a steam drum. Most usually, boiler feed water is heated in heat exchangers decoupled from the steam drum. Multiple water circuits serving different exchangers are arranged in parallel with each other and feed a single steam drum to provide a steam product of a desired pressure for which only one set of instrumentation is needed. Such steam systems are well known, and details can be added through such teachings as found in U.S. Pat. No. 7,730,854 which is incorporated herein by reference.

Energy recovery according to the present invention, often involving close temperature approaches between process fluids, is improved through the use of exchangers having enhanced nucleate boiling surface. Such enhanced boiling surface can be effected in a variety of ways as described, for example, in U.S. Pat. No. 3,384,154; U.S. Pat. No. 3,821,018; U.S. Pat. No. 4,064,914; U.S. Pat. No. 4,060,125; U.S. Pat. No. 3,906,604; U.S. Pat. No. 4,216,826; U.S. Pat. No. 3,454,081; U.S. Pat. No. 4,769,511 and U.S. Pat. No. 5,091,075; all of which are incorporated herein by reference. Such high-flux tubing is particularly suitable for the exchange of heat between the overhead of the second high-pressure xylene column and the reboiler of the first low-pressure xylene column or for the generation of steam from the xylene-column overhead.

Typically, these enhanced nucleate boiling surfaces are incorporated on the tubes of a shell-and-tube type heat exchanger. These enhanced tubes are made in a variety of different ways which are well known to those skilled in the art. For example, such tubes may comprise annular or spiral cavities extending along the tube surface made by mechanical working of the tube. Alternately, fins may be provided on the surface. In addition the tubes may be scored to provide ribs, grooves, a porous layer and the like.

Generally, the more efficient enhanced tubes are those having a porous layer on the boiling side of the tube. The porous layer can be provided in a number of different ways well known to those skilled in the art. The most efficient of these porous surfaces have what are termed reentrant cavities that trap vapors in cavities of the layer through restricted cavity openings. In one such method, as described in U.S. Pat. No. 4,064,914, the porous boiling layer is bonded to one side of a thermally conductive wall. An essential characteristic of the porous surface layer is the interconnected pores of capillary size, some of which communicate with the outer surface. Liquid to be boiled enters the subsurface cavities through the outer pores and subsurface interconnecting pores, and is heated by the metal forming the walls of the cavities. At least part of the liquid is vaporized within the cavity and resulting bubbles grow against the cavity walls. A part thereof eventually emerges from the cavity through the outer pores and then rises through the liquid film over the porous layer for disengagement into the gas space over the liquid film. Additional liquid flows into the cavity from the interconnecting pores and the mechanism is continuously repeated. Such an enhanced tube containing a porous boiling layer is commercially available under the trade name High Flux Tubing made by UOP, Des Plaines, Ill.

Figure 4:
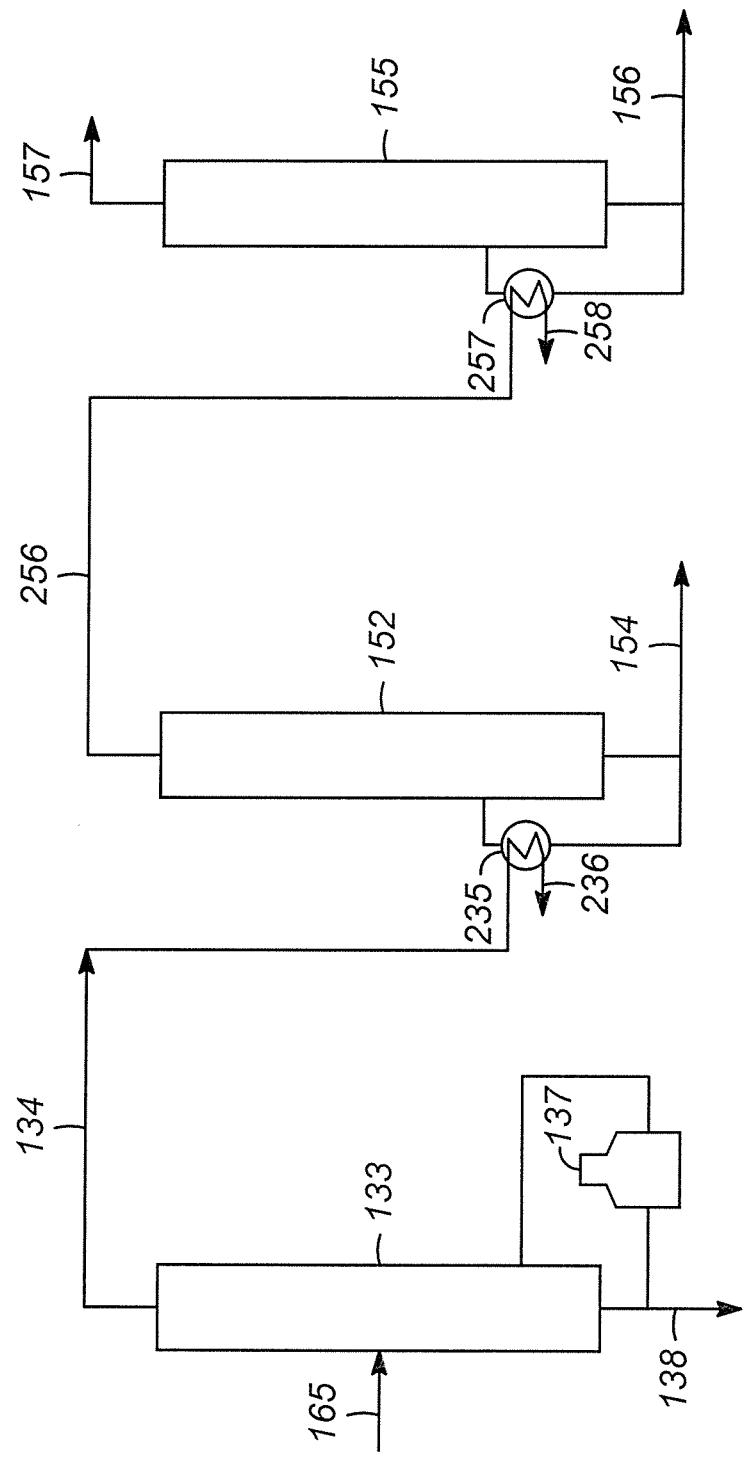
FIG. 4 illustrates examples of specific units within an aromatics complex in which direct heat exchange could achieve energy savings.

FIG. 4 illustrates examples of specific units within an aromatics complex in which direct heat exchange of overhead from one or more higher-temperature columns to reboilers of one or more lower-temperature columns could achieve energy savings, using numerical designations of processes from FIG. 2. Overhead in conduit 134 from the high-pressure xylene column 133 has a temperature sufficient to provide energy to reboil extract column 152 via reboiler 235, condensing the xylene overhead in conduit 236 for return to 133 as reflux or net overhead. The extract column may be pressurized such that overhead in conduit 256 has a sufficient temperature to reboil finishing column 155, which preferably operates at vacuum pressure, via reboiler 257, condensing extract column overhead in conduit 258. As before, the product para-xylene is recovered in conduit 156.

Figure 5:
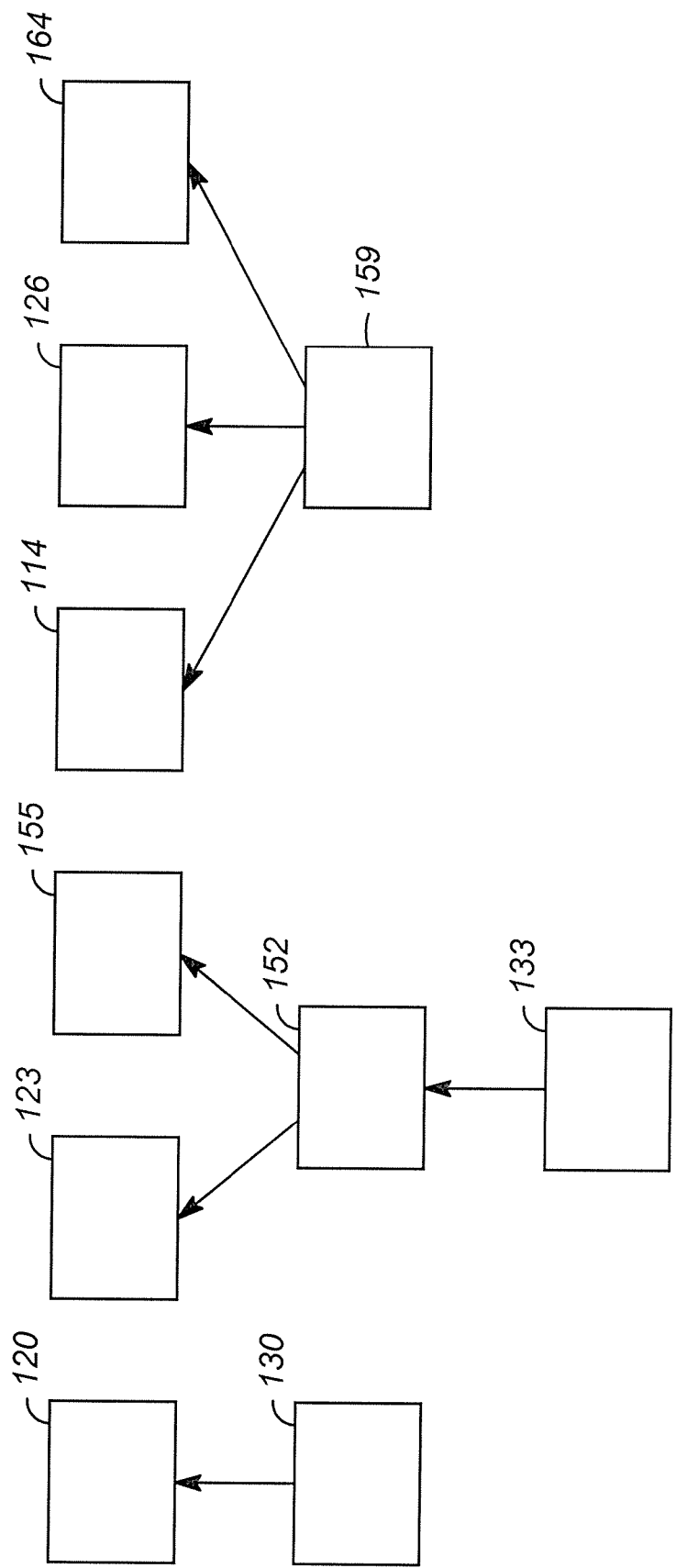
FIG. 5 illustrates an aromatics complex in which some of the energy-savings concepts described herein are applied as a supplement or substitute for other energy savings.

FIG. 5 summarizes a number, not exhaustive or exclusive, of direct heat-exchange possibilities related to FIG. 2. High-pressure xylene column 133 may provide heat to reboil one or more of low-pressure xylene column 130, extract column 152, and raffinate column 159. The low-pressure xylene column 130 may provide heat to reboil extractive distillation column 120. A pressurized extract column 152 may provide heat to reboil one or more of benzene column 123 and finishing column 155. A pressurized raffinate column 159 may provide heat to reboil one or more of reformate splitter 114, toluene column 126, and deheptanizer 164.

Figure 6:
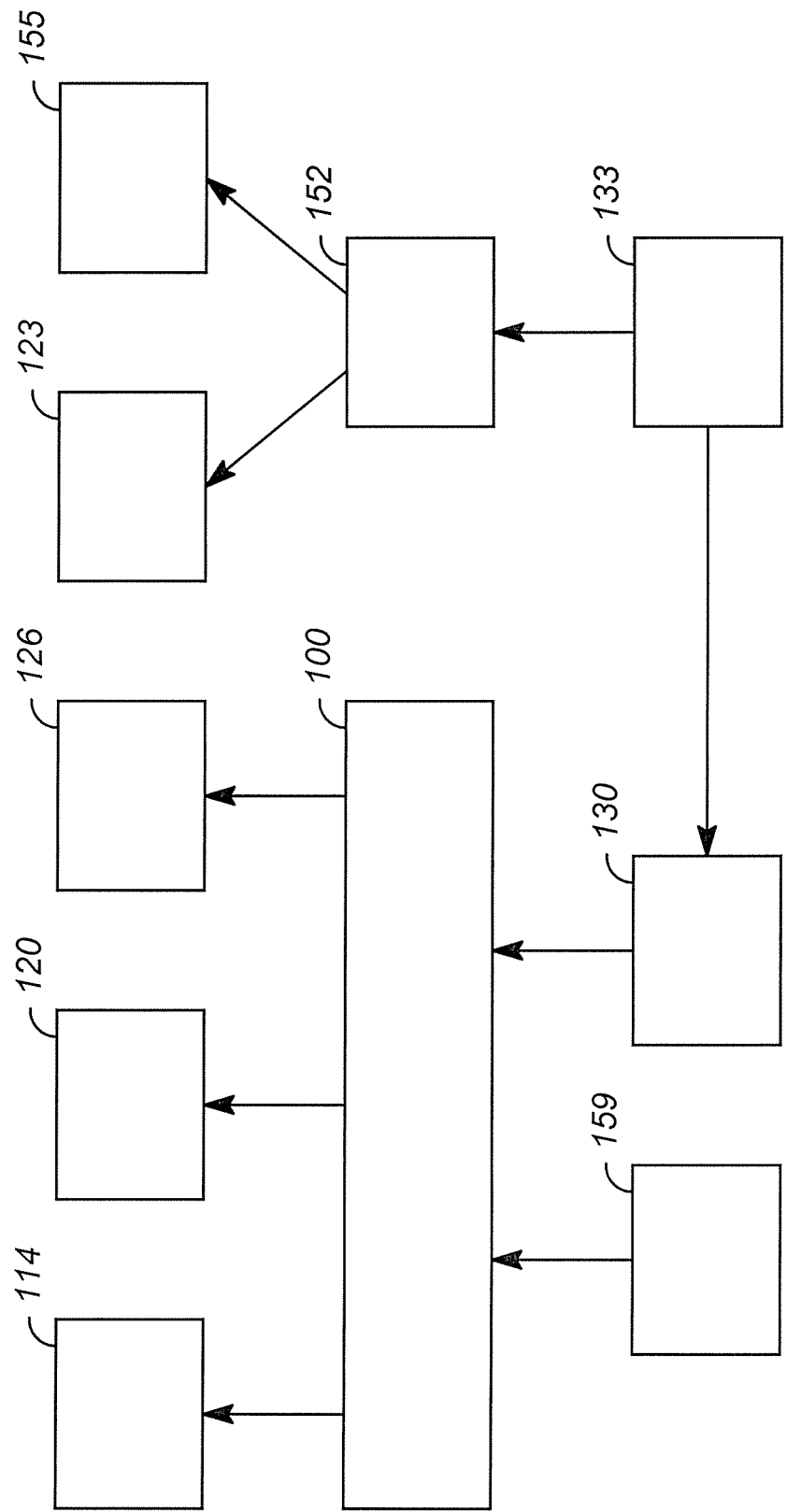
FIG. 6 illustrates the generation of steam from specific units within an aromatics complex.

FIG. 6 summarizes nonexhaustive examples of indirect heat-exchange possibilities through the generation of medium-pressure steam. Overhead streams 230 (FIG. 2) from the low-pressure xylene column 130 and 260 (FIG. 2) from the pressurized raffinate column 159 may generate medium-pressure steam in header 100 at 0.6 to 2 MPa, and preferably 0.7 to 1.5 MPa which can be used to reboil one or more of reformate splitter 114, extractive distillation column 120 and toluene column 126 with the added potential of exporting steam to other units. Such generation and usage of steam can be considered as a supplement or substitute for other energy savings such as those described in FIG. 5. For example, the high-pressure xylene column 133 may provide heat to reboil the low-pressure xylene column 130 and extract column 152, which in turn reboils the benzene column 123 and finishing column 155.

EXAMPLE

The combination of steam generation and direct heat exchange described above in FIG. 6 was evaluated in terms of payback on investment. The base case is the facility described in FIG. 1 and the case of the invention is the FIG. 6 case as applied to the flow scheme in FIG. 3. The relative key parameters for the production of para-xylene are as follows:

|  | Base Case | Invention |
|---|---|---|
| Fuel consumption | 1.0 | 0.922 |
| Net Steam consumed | 1.0 | 0 |
| generated | 1.0 | 1.35 |

The invention claimed is:

1. A process for producing one or more individual xylene isomers from feed streams containing C8 aromatics and C9-and-heavier aromatics, comprising:
   (a) a distillation process comprising two or more xylene columns separating C8-aromatics streams from a C9-and-heavier aromatics streams contained in at least one higher-boiling and at least one lower-boiling feed stream, wherein the at least one higher-boiling feed stream has a higher content of C9-and-heavier aromatics than the at least one lower-boiling feed stream, comprising distilling the at least one higher-boiling feed stream in at least one first low-pressure xylene column to separate a first C8-aromatics stream from a first C9-and-heavier aromatics stream, distilling the at least one lower-boiling feed stream in at least one second xylene column at an elevated pressure above the low pressure to separate a second C8-aromatics stream from a second C9-and-heavier aromatics stream, and condensing an overhead stream from the at least one second xylene column by exchanging heat with one or more of a reboiler of the at least one first low-pressure xylene column;
   (b) a xylene-isomer separation process to recover one or more xylene isomers from one or both of the first and second C8-aromatics streams by injecting the one or both aromatics streams and a desorbent stream into a moving-bed adsorption process to obtain a first mixture of the one or more xylene isomers and desorbent and a second mixture of non-equilibrium C8 aromatics and desorbent; and,
   (c) a desorbent-recovery process to separate the first mixture of step (b) by distillation in an extract column with a reboiler having an operating pressure of at least 300 kPa to obtain the one or more individual xylene isomers and a desorbent stream returned to the xylene isomer separation process, wherein the overhead stream of the at least one second xylene column of step (a) further exchanges heat to supply the reboiler of the extract column.

2. The process of claim 1 wherein the low pressure is between 100 and 800 kPa and the elevated pressure is about 400 kPa higher than the low pressure.

3. The process of claim 1 wherein the reboiler of the at least one first low-pressure xylene column has an enhanced nucleate boiling surface.

4. The process of claim 1 wherein the at least one lower-boiling feed stream comprises part or all of a bottoms stream from deheptanization of a C8-aromatics isomerization product.

5. The process of claim 1 wherein overhead stream from the at least one first low-pressure xylene column exchanges heat with a medium-pressure steam generator to generate steam.

6. The process of claim 1 wherein an overhead stream from the extract column of step (c) exchanges heat with a reboiler of a xylene finishing column.

7. The process of claim 6 wherein the reboiler of the xylene finishing column has an enhanced nucleate boiling surface.

8. The process of claim 1 wherein an overhead stream from the extract column of step (c) exchanges heat with a reboiler of a deheptanizer.

9. The process of claim 8 wherein the reboiler of the deheptanizer has an enhanced nucleate boiling surface.

10. The process of claim 1, wherein the one or more individual xylene isomers includes para-xylene.

* * * * *